(12) United States Patent
Liu

(10) Patent No.: US 11,142,627 B2
(45) Date of Patent: Oct. 12, 2021

(54) INSULATION LAYER COMPOSITION AND INSULATION LAYER FOR PLANT TISSUE CULTURE

(71) Applicant: Jun-Nan Liu, Yilan County (TW)

(72) Inventor: Jun-Nan Liu, Yilan County (TW)

( * ) Notice: Subject to any disclaimer, the term of this patent is extended or adjusted under 35 U.S.C. 154(b) by 273 days.

(21) Appl. No.: 16/566,902

(22) Filed: Sep. 11, 2019

(65) Prior Publication Data

US 2020/0079928 A1 Mar. 12, 2020

(30) Foreign Application Priority Data

Sep. 12, 2018 (TW) .................................. 107132120

(51) Int. Cl.
*C09D 131/04* (2006.01)
*C08K 5/00* (2006.01)
*C08B 37/08* (2006.01)

(52) U.S. Cl.
CPC ........ *C08K 5/0058* (2013.01); *C08B 37/0072* (2013.01); *C09D 131/04* (2013.01)

(58) Field of Classification Search
None
See application file for complete search history.

(56) References Cited

U.S. PATENT DOCUMENTS

| | | | | |
|---|---|---|---|---|
| 10,471,036 B2* | 11/2019 | Scholz | ..................... | A61P 27/16 |
| 2002/0155962 A1* | 10/2002 | Cincotta | ................... | A61K 8/86 |
| | | | | 510/119 |
| 2005/0058673 A1* | 3/2005 | Scholz | ................... | A61K 47/12 |
| | | | | 424/401 |
| 2005/0089539 A1* | 4/2005 | Scholz | ................... | A61K 47/10 |
| | | | | 424/401 |
| 2011/0190424 A1* | 8/2011 | Yang | ....................... | C12P 19/04 |
| | | | | 524/27 |
| 2012/0052234 A1* | 3/2012 | Natarajan | ............... | B29C 33/52 |
| | | | | 428/99 |
| 2013/0303615 A1* | 11/2013 | Scholz | ................. | A61K 9/0043 |
| | | | | 514/552 |
| 2014/0369953 A1* | 12/2014 | Purschwitz | ............ | A01N 31/16 |
| | | | | 424/78.36 |
| 2015/0335872 A1* | 11/2015 | Yang | .................... | A61B 17/064 |
| | | | | 604/46 |

FOREIGN PATENT DOCUMENTS

CN 1878536 B 11/2014

OTHER PUBLICATIONS

Google Scholar keyword search (Year: 2021).*

\* cited by examiner

*Primary Examiner* — Peter A Salamon
(74) *Attorney, Agent, or Firm* — CKC & Partners Co., LLC

(57) ABSTRACT

The present disclosure provides an insulation layer composition and an insulation layer for a plant tissue culture. The insulation layer composition includes polyvinyl acetate emulsion resin, water, a gel forming agent and a hyaluronic acid diluent, in which the gel forming agent is a mixture of glycerin and polyglycerol acrylate. The insulation layer for the plant tissue culture includes the insulation layer composition.

10 Claims, 15 Drawing Sheets
(15 of 15 Drawing Sheet(s) Filed in Color)

INSULATION LAYER COMPOSITION AND INSULATION LAYER FOR PLANT TISSUE CULTURE

RELATED APPLICATIONS

This application claims priority to Taiwan Application Ser. No. 107132120, filed Sep. 12, 2018, which is herein incorporated by reference.

BACKGROUND

Technical Field

The present disclosure relates to a composition and an insulation layer. More particularly, the present disclosure relates to an insulation layer composition and an insulation layer for a plant tissue culture.

Description of Related Art

Plant tissue culture is a technique in which part of cells or tissues of a plant body are separated from the mother plant and cultured under appropriate conditions to enable them to grow, develop, differentiate and proliferate. The principle of plant tissue culture is that plant cells have the ability to multipotent differentiation, that is, a certain type of cells in plants can develop independently and differentiate into intact plant bodies. Plant tissue culture can produce a large number of plants with a small amount of mother plant, so that plant tissue culture can be used for many purposes, such as basic botany and genetic studies, as well as agricultural breeding and variety retention.

Microbial infection is the most common cause of culture failure in plant tissue culture. Generally, plant tissue culture needs to be carried out on a laminar airflow bench, and all equipment, such as tweezers and culture flasks, need to be sterilized or disinfected to prevent the tissue to be cultured from being infected by bacteria and fungi. In addition to equipment, if the plant tissue to be cultivated is from plants that are generally grown outdoors, these plant tissues also need to be disinfected with disinfectant water. The water used in the operation of the plant tissue culture is also need to be sterilized distilled water.

In order to ensure that the tissue culture plants in the tissue culture flask are not infected with microorganisms and the tissue culture flasks are maintained in a sterile state, the manipulated tissue culture plants are usually sealed in tissue culture flasks to isolate external microorganisms. However, plants need oxygen and carbon dioxide to improve their growth. It is very difficult for tissue culture plants to grow healthy in a limited confined space. A small amount of ethylene is also released during the growth of the plant. When ethylene accumulates to a certain concentration, it will have a negative effect on the growth of the plant. Therefore, air permeability in the limited confined space is very important for tissue culture of plants. In addition, moisture or water droplets are easily accumulated in the tissue culture bottle in a closed environment to maintain certain humidity, which is an appropriate environment for microbial growth. Therefore, microorganisms that are incompletely sterilized in the tissue culture bottle may grow to cause contamination of the tissue culture plants.

SUMMARY

According to one aspect of the present disclosure, an insulation layer composition is provided. The insulation layer composition includes a polyvinyl acetate emulsion resin, water, a gel forming agent and a hyaluronic acid diluent. The gel forming agent is a mixture of glycerin and polyglycerol acrylate.

According to another aspect of the present disclosure, an insulation layer for a plant tissue culture is provided. The insulation layer for a plant tissue culture includes the insulation layer composition according to the aforementioned aspect.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

Figure 1:
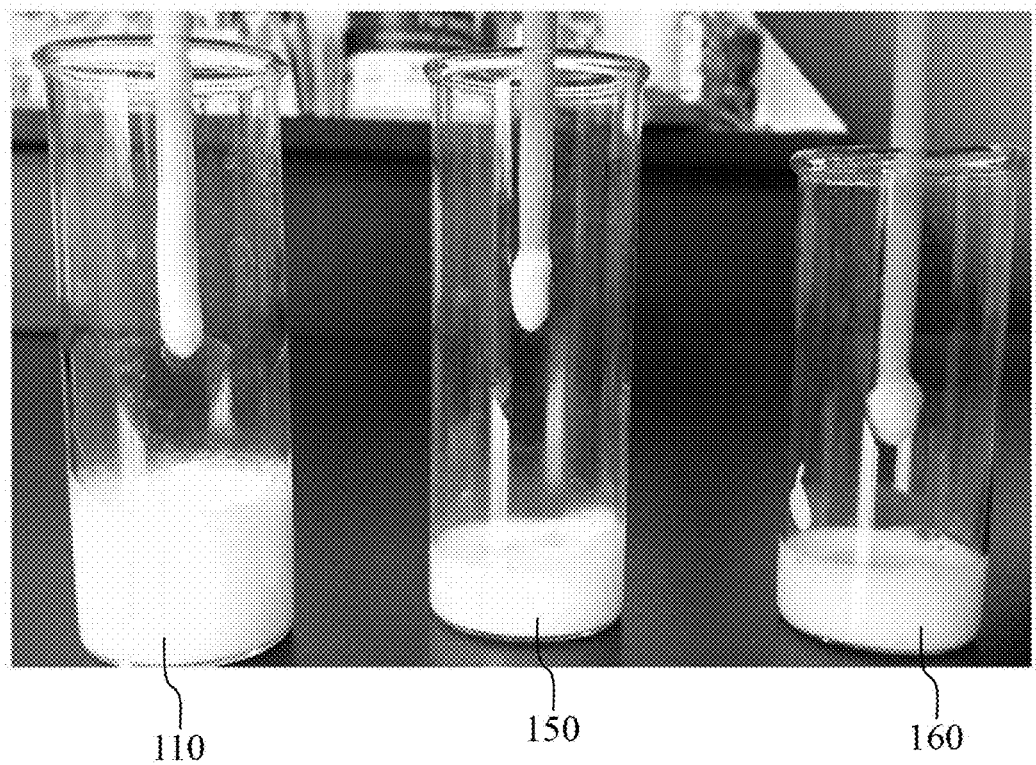
FIG. 1 shows the solidification state of Example 1 insulation layer composition of the present disclosure on the 10th day and the solidification state of Example 5 insulation layer composition of the present disclosure and Example 6 insulation layer composition of the present disclosure on the 4th day.

An insulation layer composition is provided in the present disclosure. The insulation layer composition includes a polyvinyl acetate emulsion resin, water, a gel forming agent and a hyaluronic acid diluent, wherein the gel forming agent is a mixture of glycerin and polyglycerol acrylate. Preferably, the gel forming agent can be Hispagel 200, which is a mixture of glycerin and polyglyceryl acrylate manufactured by Hispano Quimica S.A. A volume percent concentration (V/V) of the hyaluronic acid diluent can be 1%.

Polyvinyl acetate resin (PVAc) is a thermoformable long-chain polymer resin obtained by addition polymerization of vinyl acetate (VAc), wherein the polymerization is a free radical polymerization. The vinyl acetate monomer is slightly soluble in water, and the polyvinyl acetate resin formed by further polymerization is insoluble in water. Therefore, a resin emulsion is formed by emulsion polymerization for obtaining a water-based glue. The reaction system contains an oil-soluble polyvinyl acetate resin monomer, an emulsifier (surfactant; protective colloid), a reaction initiator, and water (dispersion phase) to obtain a polyvinyl acetate emulsion resin. The solidification is carried out by evaporation of the water from the glue and drying and hardening to form a film, so that it can be solidified at room temperature without adding a hardener.

According to the aforementioned insulation layer composition, the polyvinyl acetate emulsion resin, the water, the gel forming agent and the hyaluronic acid diluent can be mixed in a weight ratio of 2:1:0.5:0.5 to 2:2:1:1. Preferably, the polyvinyl acetate emulsion resin, the water, the gel forming agent and the hyaluronic acid diluent can be mixed in a weight ratio of 2:1:0.5:1, a weight ratio of 2:1:0.5:0.5 or a weight ratio of 2:1.5:0.7:0.6.

An insulation layer for a plant tissue culture is further provided in the present disclosure. The insulation layer includes the aforementioned insulation layer composition, wherein the insulation layer composition has good insulation effect. The insulation layer can cover the medium of the plant tissue culture and can be used to isolate the medium from contact with the source of contamination, and the source of the contamination can be a microorganism. Preferably, the microorganism can be a fungus or a bacterium. Thereby, the plants tissue culture can be cultured without being contaminated by bacteria or fungi in an open space.

The present disclosure will be further exemplified by the following specific embodiments so as to facilitate utilizing and practicing the present disclosure completely by the people skilled in the art without over-interpreting and over-experimenting. However, the readers should understand that the present disclosure should not be limited to these practical details thereof, that is, these practical details are used to describe how to implement the materials and methods of the present disclosure and are not necessary.

EXAMPLE AND COMPARATIVE EXAMPLE

Examples 1-6

As described above, the present disclosure is directed to providing the insulation layer composition useful as the insulation layer for plant tissue culture, wherein the insulation layer composition includes the polyvinyl acetate emulsion resin, water, the gel forming agent, and the hyaluronic acid diluent. Specifically, Example 1 insulation layer composition 110, Example 2 insulation layer composition 120, Example 3 insulation layer composition 130, Example 4 insulation layer composition 140, Example 5 insulation layer composition 150 and Example 6 insulation layer composition 160 is prepared in the mixing ratio of the polyvinyl acetate emulsion resin, the water, the gel forming agent, and the hyaluronic acid diluent shown in Table 1, respectively. The gel forming agent used is Hispagel 200, and the volume percent concentration (V/V) of the hyaluronic acid diluent used is 1%.

TABLE 1

| | polyvinyl acetate emulsion resin | water | gel forming agent | hyaluronic acid diluent |
|---|---|---|---|---|
| Example 1 | 2 | 1 | — | 0.5 |
| Example 2 | 2 | 1 | 1 | — |
| Example 3 | 2 | 2 | 1 | — |
| Example 4 | 2 | 1 | 1 | 0.5 |
| Example 5 | 2 | 1 | 0.5 | 1 |
| Example 6 | 2 | 1 | 0.5 | 0.5 |

After the preparation on the 1st day, the viscosity state is used to evaluate the state of each of examples and whether it can be used as the insulation layer for the plant tissue culture. If the viscosity after the preparation is low, it will be solidified for a longer period of time. In the test results, Example 1 insulation layer composition 110 has a low viscosity and is in a liquid state. Example 2 insulation layer composition 120, Example 3 insulation layer composition 130 and Example 4 insulation layer composition 140 have higher viscosity and are in the solid state that is too hard to operate. On the other hand, Example 5 insulation layer composition 150 and Example 6 insulation layer composition 160 have a moderate viscosity and are in the paste state. The viscosity of Example 5 insulation layer composition 150 is less than that of Example 6 insulation layer composition 160.

Please refer to FIG. 1, which shows the solidification state of Example 1 insulation layer composition 110 on the 10th day and the solidification state of Example 5 insulation layer composition 150 and Example 6 insulation layer composition 160 on the 4th day. The results of the solidification state of Example 2 insulation layer composition 120, Example 3 insulation layer composition 130, and Example 4 insulation layer composition 140 are not shown. The solidification state is determined by inserting the disposable chopstick into Examples 1-6 of insulation layer composition, and then taking up the disposable chopsticks and observing the adhesion amount. The solidification state is for observing whether Example 1 insulation layer composition 110, Example 5 insulation layer composition 150 and Example 6 insulation layer composition 160, has a higher viscosity after solidification and does not flow arbitrarily after pouring. In FIG. 1, Example 1 insulation layer composition 110 is still in the liquid state after the solidification for 10 days, and Example 5 insulation layer composition 150 and Example 6 insulation layer composition 160 are in the paste state after the solidification for 4 days. However, Example 5 insulation layer composition 150 still moves slowly when poured, and Example 6 insulation layer composition 160 is solidified without arbitrarily flowing, and the amount of adhesion of Example 6 insulation layer composition 160 is significantly greater than that of Example 1 insulation layer composition 110 and Example 5 insulation layer composition 150. Therefore, Example 6 insulation layer composition 160 is used for performing the isolation microbial growth test.

The medium used for the isolation microbial growth test is a ½ MS semi-solid medium using MS (Murashige and Skoog 1962) basic salt formula with a nitrogen content of ½, in which the major elements include 950 mg/l of $KNO_3$, 440 mg/l of $CaCl_2 \cdot 2H_2O$, 185 mg/l of $MgSO_4 \cdot 7H_2O$ and 85 mg/l of $KH_2PO_4$, and the minor elements include 0.265 mg/l of KI, 3.1 mg/l of $H_3BO_3$, 11.15 mg/l of $MnSO_4 \cdot 4H_2O$, 4.3 mg/l of $ZnSO_4 \cdot 7H_2O$, 0.125 mg/l of $Na_2MoO_4 \cdot 2H_2O$, 0.0125 mg/l of $CuSO_4 \cdot 5H_2O$ and 0.0125 mg/l of $CoCl_2 \cdot 6H_2O$. The iron salts include 13.9 mg/l of $FeSO_4 \cdot 7H_2O$ and 18.65 mg/l of $NaEDTA \cdot 2H_2O$. Other supplements include 50 mg/l of inositol, 0.25 mg/l of Nicotinic acid, 0.25 mg/l of pyridoxin, 0.05 mg/l of Thiamine-HCL, 1 mg/l of glycine and 3% agarose. The plant material is a Haworthia succulent sterile seedling, and all operations of the plant tissue culture are performed in the laminar airflow bench. The test procedure is as follows: the plant material is implanted in the medium for use, and the test group includes 8 tubes, in which each of the tube is implanted into one plant material. Then, the polyvinyl acetate emulsion resin, water, gel forming agent and hyaluronic acid diluent are uniformly mixed in the weight ratio of 2:1:0.5:0.5 to prepare the insulation layer composition of the present disclosure (Example 6 insulation layer composition 160). Example 6 insulation layer composition 160 is then poured into the tube to a thickness of about 0.5 cm so that Example 6 insulation layer composition 160 can sufficiently cover the surface of the medium to form an insulation layer. The tissue culture plants covered with Example 6 insulation layer composition 160 are placed in an open space to perform the isolate the microbial growth test, and photographed on the 1st day, the 30th day, and the 63rd day to observe when microorganisms began to grow. Further, the medium for plant tissue culture and Example 6 insulation layer composition 160 are observed to have a shrinkage phenomenon on the 30th day. In order to maintain the thickness of the medium and Example 6 insulation layer composition 160, a small amount of tap water is added to each test group on the 30th day of the test. The test also includes the control group, which is ½ MS semi-solid medium without any antibacterial conditions, and the control group includes 3 tubes (control group 210, control group 220 and control group 230). The control group is also placed in the open space for isolation microbial growth test to observe when microorganisms began to grow.

Figure 2A:
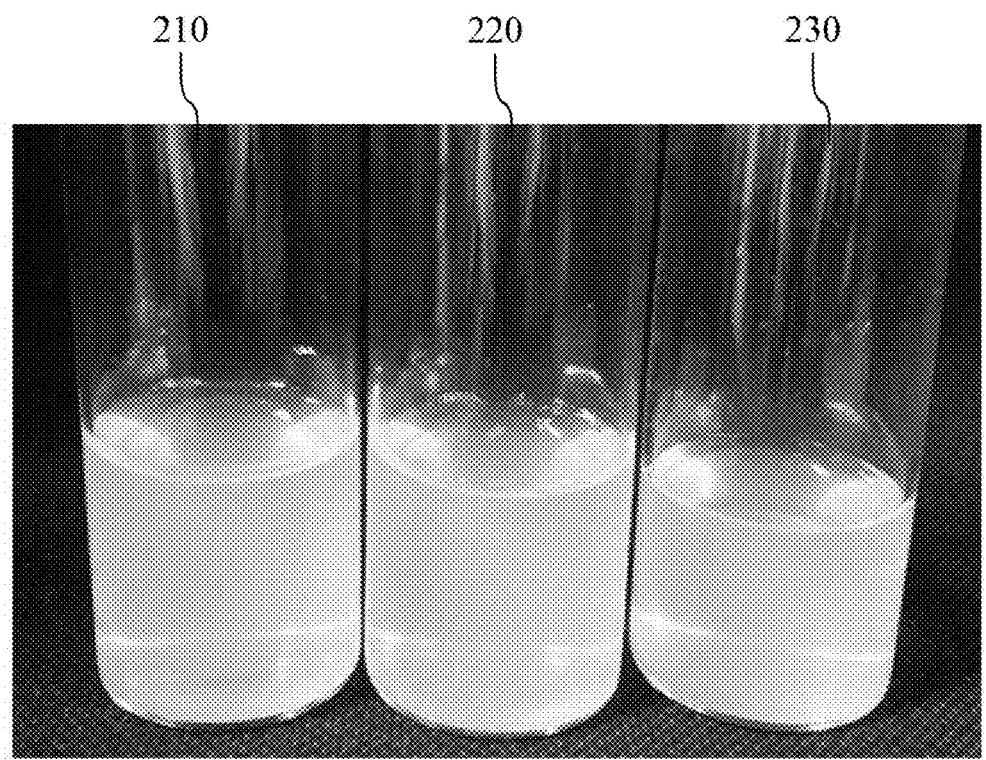
FIGS. 2A and 2B show test results of the isolation microbial growth test in the control group.
Figure 2B:
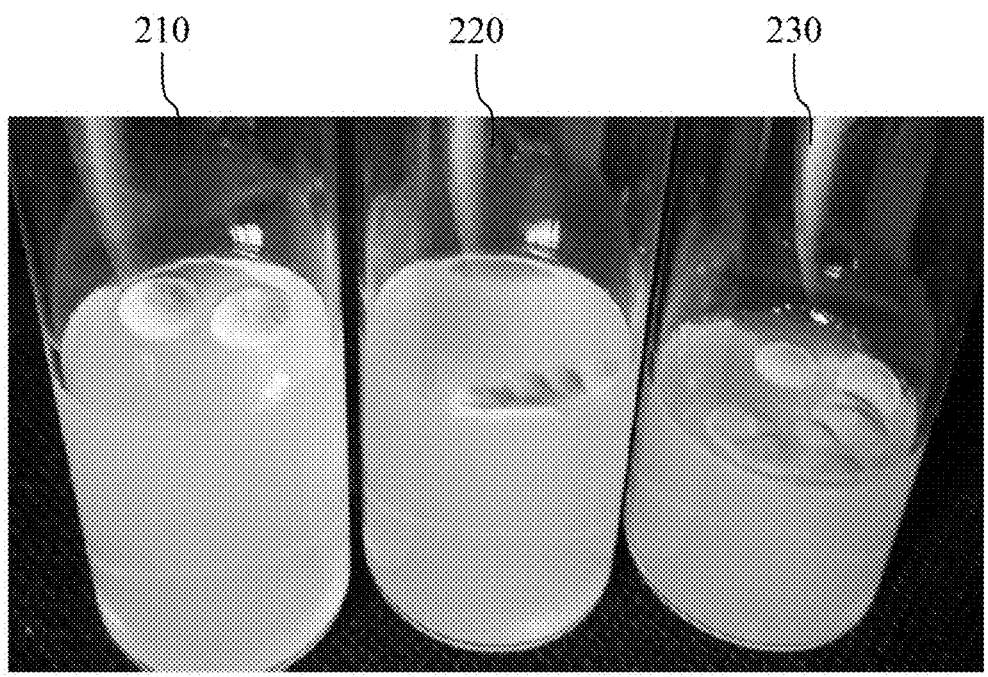
Figure 3A:
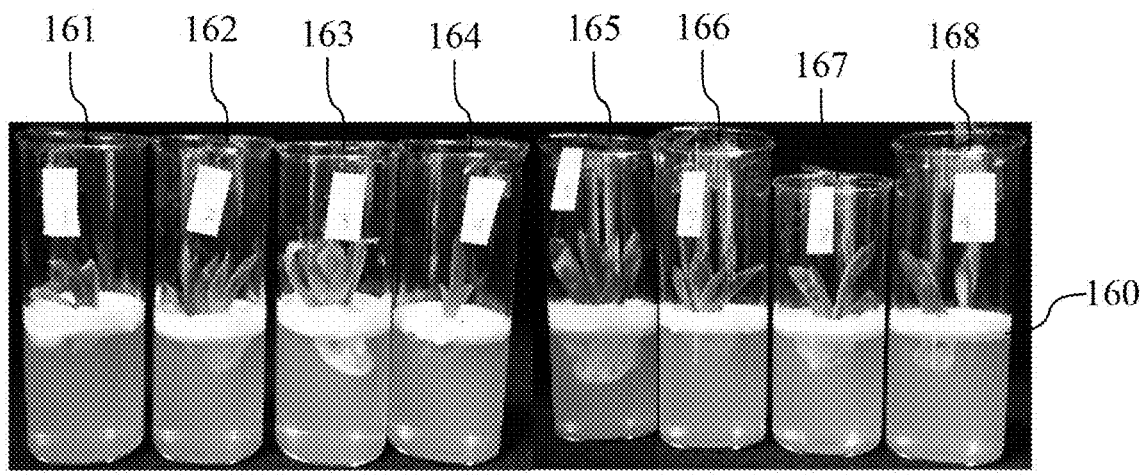
FIGS. 3A, 3B, 3C and 3D show test results of the isolation microbial growth test according to Example 6 of one embodiment of the present disclosure.
Figure 3B:
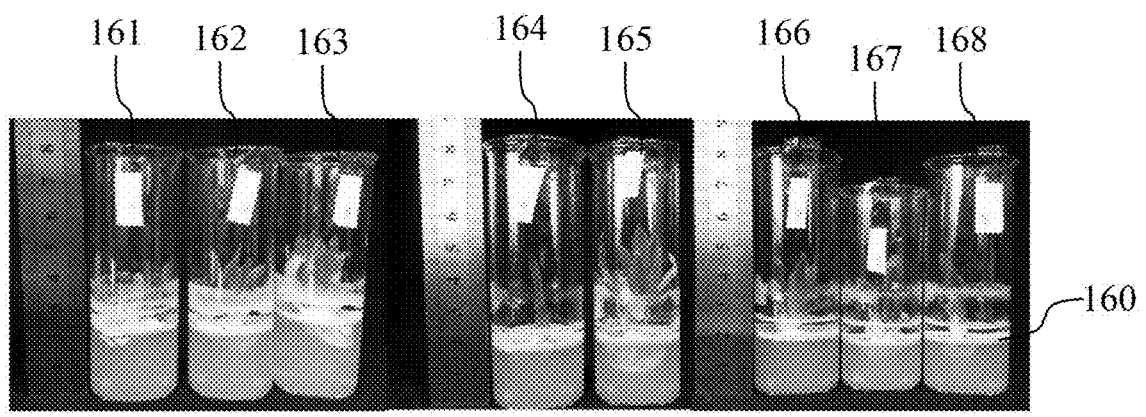
Figure 3C:
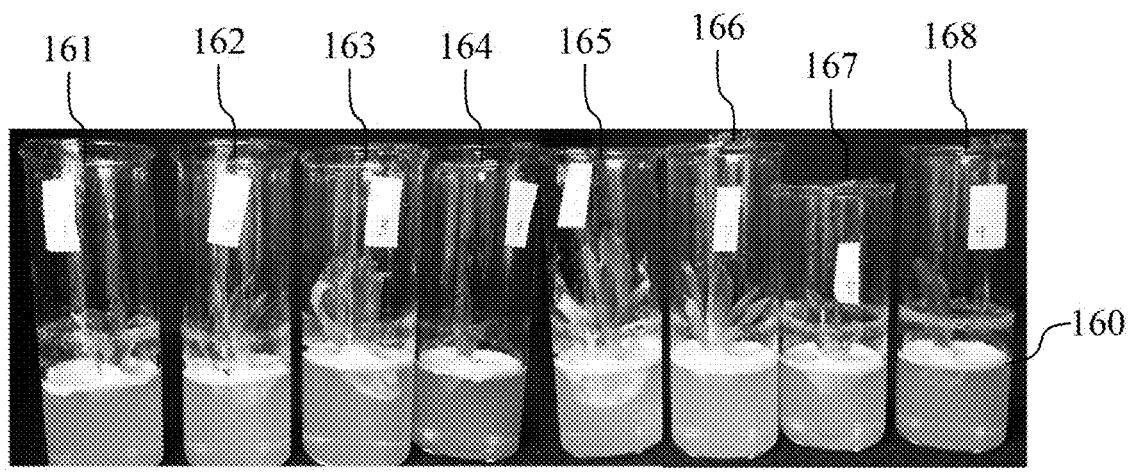
Figure 3D:
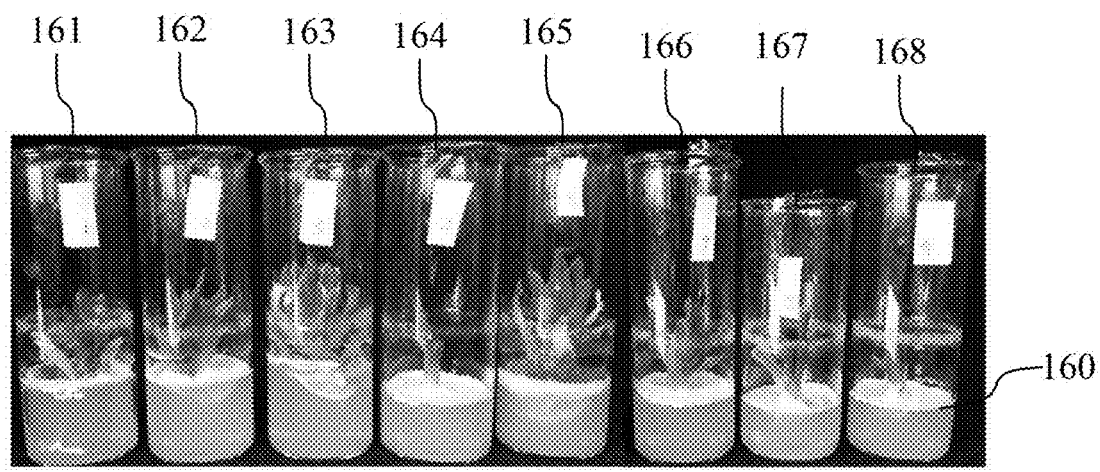

Please refer to FIGS. 2A, 2B, 3A, 3B, 3C and 3D. FIGS. 2A and 2B show test results of the isolation microbial growth test in the control group. In FIGS. 2A and 2B, the tubes from left to right are the control group 210, the control group 220, and the control group 230, respectively, wherein FIG. 2A shows the test result on the 1st day, and FIG. 2B shows the test result on the 4th day. FIGS. 3A to 3D show test results of the isolation microbial growth test according to Example 6 insulation layer composition 160. In FIGS. 3A to 3D, the tubes from left to right are Example 6 insulation layer composition test group 161, Example 6 insulation layer composition test group 162, Example 6 insulation layer composition test group 163, Example 6 insulation layer composition test group 164, Example 6 insulation layer composition test group 165, Example 6 insulation layer composition test group 166, Example 6 insulation layer composition test group 167 and Example 6 insulation layer composition test group 168, wherein FIG. 3A shows the test result on the 1st day, FIG. 3B shows the test result before adding tap water on the 30th day, FIG. 3C shows the test result after adding tap water on the 30th day, and FIG. 3D shows the test result on the 63rd day.

In FIG. 2B, a mildew condition can be observed in the control group 210, the control group 220, and the control group 230 without antibacterial conditions on the 4th day, and according to the mildew condition, it presumed that the condition of mold growth should start from the 2nd day to the 3rd day. In FIGS. 3B to 3D, the microbial growth cannot be observed in Example 6 insulation layer composition test group 161, Example 6 insulation layer composition test group 162, Example 6 insulation layer composition test group 163, Example 6 insulation layer composition test group 164, Example 6 insulation layer composition test group 165, Example 6 insulation layer composition test group 166, Example 6 insulation layer composition test group 167 and Example 6 insulation layer composition test group 168 on the 30th day and the 63rd day. The results indicate that the insulation layer composition of the present disclosure can be used as the insulation layer for plant tissue culture, allowing tissue culture plants to grow in the open space and effectively avoiding bacterial or fungal contamination. The results of FIGS. 3B and 3C show that after adding tap water, the medium of the plant tissue culture can restore to its original thickness, but Example 6 insulation layer composition 160 cannot be restored to its original thickness.

Example 7

The aforementioned results indicate that Example 6 insulation layer composition 160 can be used as the insulation layer for plant tissue culture, and the medium will shrink obviously on the 36th day and the 39th day. It is speculated that the reason may be that the water of the medium and Example 6 insulation layer composition 160 are evaporated due to evapotranspiration, or the roots of the plant absorb nutrients or water to lose water. Therefore, in this test example, in order to improve the shrinkage phenomenon of the medium, the polyvinyl acetate emulsion resin, water, gel forming agent and hyaluronic acid diluent are uniformly mixed in a weight ratio of 2:1.5:0.7:0.6 to prepare the insulation layer composition of the present disclosure (Example 7 insulation layer composition 170). The gel forming agent used in this test example is Hispagel 200, and the volume percent concentration (V/V) of the hyaluronic acid diluent used in this test example is 1%. Example 7 insulation layer composition 170 is then poured into the tube to a thickness of about 0.5 cm so that Example 7 insulation layer composition 170 can sufficiently cover the surface of the medium to form the insulation layer, and the test group includes 9 tubes. The tissue culture plants covered with Example 7 insulation layer composition 170 are placed in the open space to perform the isolate the microbial growth test, and photographed on the 1st day, the 22nd day, and the 43rd day to observe when microorganisms began to grow.

Figure 4A:
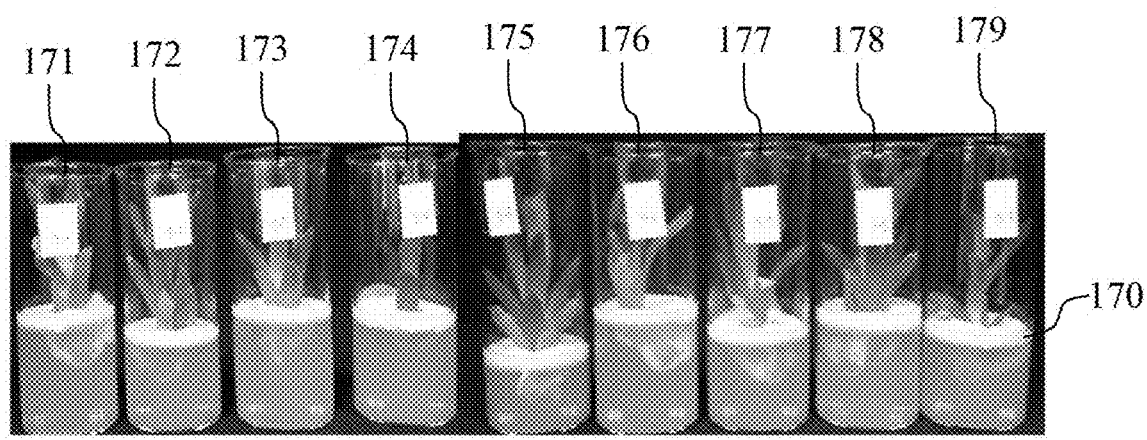
FIGS. 4A, 4B and 4C show test results of the isolation microbial growth test according to Example 7 of one embodiment of the present disclosure.
Figure 4B:
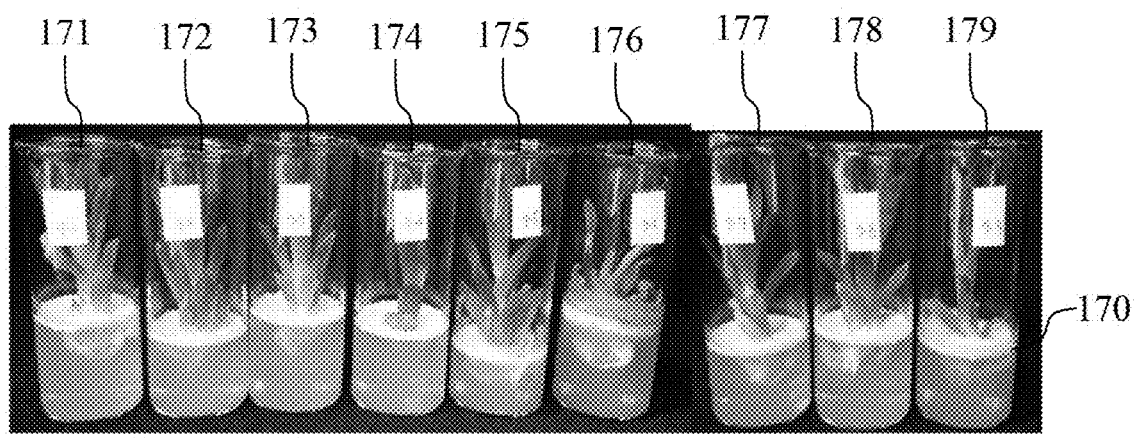
Figure 4C:
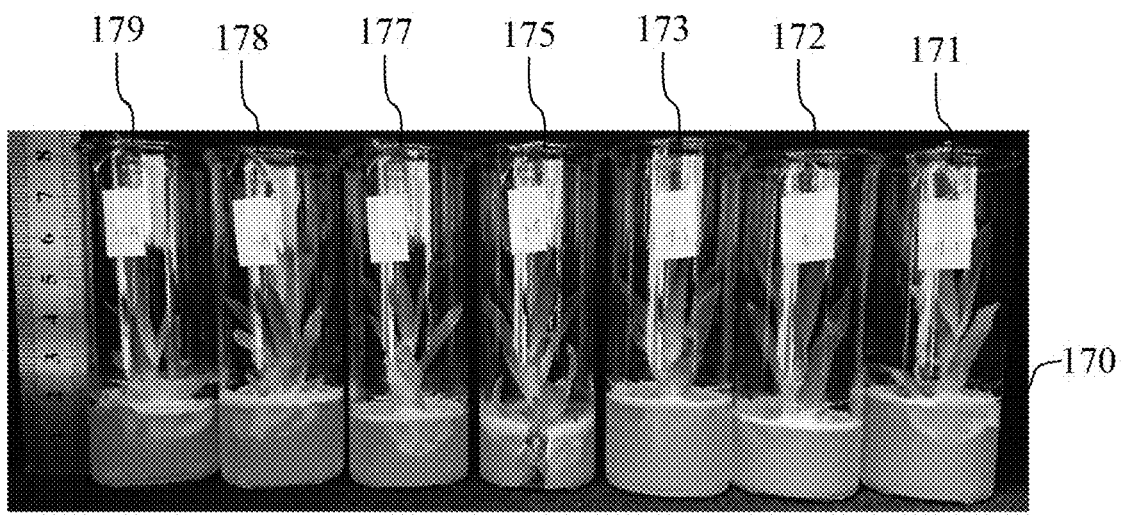

Please refer to FIGS. 4A, 4B and 4C, which show test results of the isolation microbial growth test according to Example 7 insulation layer composition 170. In FIGS. 4A and 4B, the tubes from left to right are Example 7 insulation layer composition test group 171, Example 7 insulation layer composition test group 172, Example 7 insulation layer composition test group 173, Example 7 insulation layer composition test group 174, Example 7 insulation layer composition test group 175, Example 7 insulation layer composition test group 176, Example 7 insulation layer composition test group 177, Example 7 insulation layer composition test group 178, and Example 7 insulation layer composition test group 179, wherein FIG. 4A shows the test result on the 1st day, and FIG. 4B shows the test result on the 22nd day. In FIG. 4C, the tubes from left to right are Example 7 insulation layer composition test group 179, Example 7 insulation layer composition test group 178, Example 7 insulation layer composition test group 177, Example 7 insulation layer composition test group 175, Example 7 insulation layer composition test group 173, Example 7 insulation layer composition test group 172, and Example 7 insulation layer composition test group 171, and FIG. 4C shows the test result on the 43rd day. In FIG. 4B, the microbial growth cannot be observed in Example 7 insulation layer composition test group 171, Example 7 insulation layer composition test group 172, Example 7 insulation layer composition test group 173, Example 7 insulation layer composition test group 174, Example 7 insulation layer composition test group 175, Example 7 insulation layer composition test group 176, Example 7 insulation layer composition test group 177, Example 7 insulation layer composition test group 178, and Example 7 insulation layer composition test group 179 on the 22nd day, and the medium is only slightly reduced. In FIG. 4C, the microbial growth cannot be observed in Example 7 insulation layer composition test group 171, Example 7 insulation layer composition test group 172, Example 7 insulation layer composition test group 173, Example 7 insulation layer composition test group 175, Example 7 insulation layer composition test group 177, Example 7 insulation layer composition test group 178, and Example 7 insulation layer composition test group 179 on the 43rd day. Although the height of the medium is decreased by 0.5 cm to 0.7 cm, the condition of the medium is not cracked. The cleavage condition of the medium of Example 7 insulation layer composition test group 175 is because the long side buds are stretched rather than cracked. The result indicates that the insulation layer composition of the present disclosure can be used as the insulation layer for plant tissue culture, allowing tissue culture plants to grow in the open space, effectively avoiding bacterial or fungal contamination, and effectively improving the cracked condition of the tissue culture medium in the tissue culture.

COMPARATIVE EXAMPLE

In this test, Clorox colloid is used as a comparative insulation layer in plant tissue culture as a comparative example, and the isolation microbial growth test is further performed. Clorox colloids are prepared by formulating 5%, 10%, and 15% Clorox (NaOCl) solutions in sterile water, and then adding 1% agar to form 5% Clorox colloid (Comparative Example 1), 10% Clorox colloid (Comparative Example 2) and 15% Clorox colloid (Comparative Example 3). The plant material is the Haworthia succulent sterile seedling, and all operations of the plant tissue culture are performed in the laminar airflow bench. The test procedure is as follows: ½ MS semi-solid medium are poured into the sterilized tube, and after the ½ MS semi-solid medium is solidified, Comparative Example 1, Comparative Example 2, and Comparative Example 3 is poured into the tube with a thickness about 1 to 1.5 cm, respectively, for sufficiently covering the surface of the medium to form the Comparative Example insulation layer 310. The plant material is implanted in the medium 2 days after Clorox colloid solidification, and the test group includes 9 tubes, in which each of the tube is implanted into one plant material. The tissue culture plants covered with Comparative Example 1, Comparative Example 2 or Comparative Example 3 are placed in the open space to perform the isolate the microbial growth test, and photographed on the 1st day and the 28th day to observe when microorganisms began to grow.

Figure 5A:
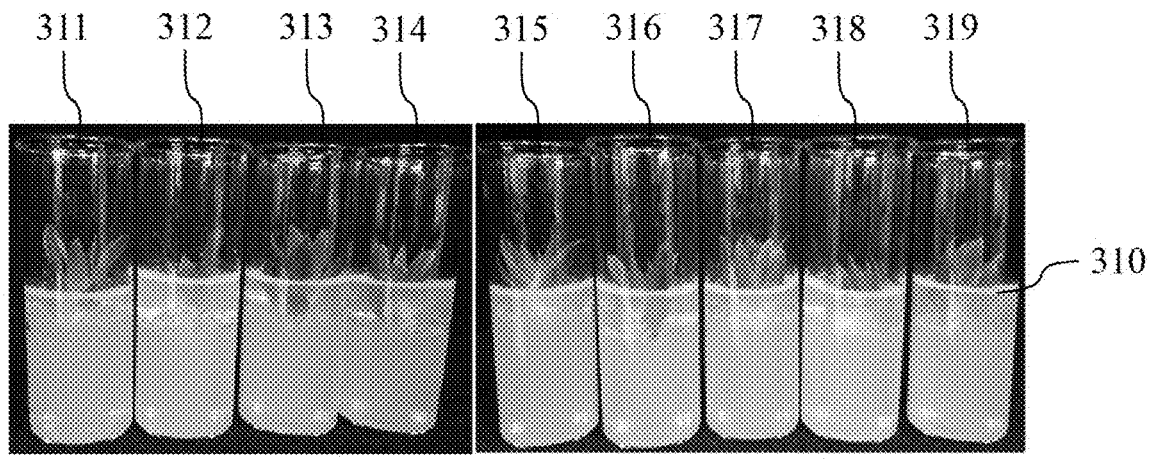
FIGS. 5A and 5B show test results of the isolation microbial growth test according to Comparative Example 3 of the present disclosure.
Figure 5B:
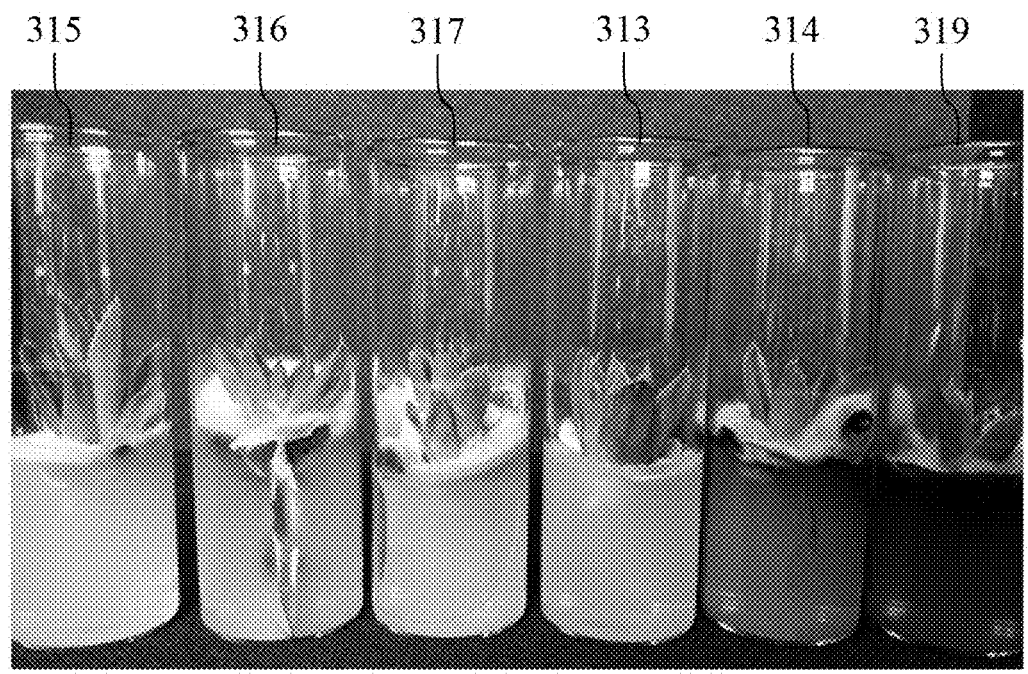

The tissue culture plants which used Comparative Example 1 and Comparative Example 2 as the insulation layers began to develop microbial growth on the 3rd and 4th day, respectively. In tissue culture plants used Comparative Example 3 as the insulation layer, 3 tubes of the tissue culture plants were found to have microbial growth on the 10th day, 6 tubes of the tissue culture plants were found to have microbial growth on the 12th day, and 8 tubes of the tissue culture plants were found to have microbial growth on the 15th day. Please further refer to FIGS. 5A and 5B, which show test results (6 tubes in 9 tubes) of the isolation microbial growth test according to Comparative Example 3 of the present disclosure. FIG. 5A shows the test result on the 1st day, the tubes from left to right are Comparative Example 3 test group 311, Comparative Example 3 test group 312, Comparative Example 3 test group 313, Comparative Example 3 test group 314, Comparative Example 3 test group 315, Comparative Example 3 test group 316, Comparative Example 3 test group 317, Comparative Example 3 test group 318, and Comparative Example 3 test group 319. FIG. 5B shows the test result on the 28th day, the tubes from left to right are Comparative Example 3 test group 315, Comparative Example 3 test group 316, Comparative Example 3 test group 317, Comparative Example 3 test group 313, Comparative Example 3 test group 314, and Comparative Example 3 test group 319. On the 28th day, the microbial contamination condition can be observed in Comparative Example 3 test group 315, Comparative Example 3 test group 316, Comparative Example 3 test group 317, Comparative Example 3 test group 313, Comparative Example 3 test group 314, and Comparative Example 3 test group 319. The results show that Clorox, a commonly used disinfectant for plant tissue culture, is still not effective in inhibiting microbial growth as the insulation layer.

Examples 8-9

In this test example, the plant materials are orchid parent seedling and orchid seedling, and all operations of the plant tissue culture are performed in the laminar airflow bench. The medium used for the isolation microbial growth test is a ½ MS semi-solid medium with 3% sugar and 0.75% agarose. The test procedure is as follows: the plant material is implanted in the medium for use, and the test group includes 3 tubes, in which each of the tube is implanted into one plant material. Then, the polyvinyl acetate emulsion resin, water, gel forming agent and hyaluronic acid diluent are uniformly mixed in the weight ratio of 2:1:0.5:0.5 to prepare the insulation layer composition of the present disclosure (Example 8 insulation layer composition 410 and Example 9 insulation layer composition 420). Example 8 insulation layer composition 410 is then poured into the tube with orchid parent seedling to the thickness of about 0.2 cm to 0.3 cm so that Example 8 insulation layer composition 410 can sufficiently cover the surface of the medium to form the insulation layer. Example 9 insulation layer composition 420 is then poured into the tube with orchid seedling to the thickness of about 0.2 cm to 0.3 cm so that Example 9 insulation layer composition 420 can sufficiently cover the surface of the medium to form the insulation layer. The tissue culture plants covered with Example 8 insulation layer composition 410 or Example 9 insulation layer composition 420 are placed in the open space with temperature range of 26° C. to 27° C. to perform the isolate the microbial growth test, and photographed on the 1st day, the 8th day, the 15th day, the 22nd day and the 29th day to observe when microorganisms began to grow.

Figure 6A:
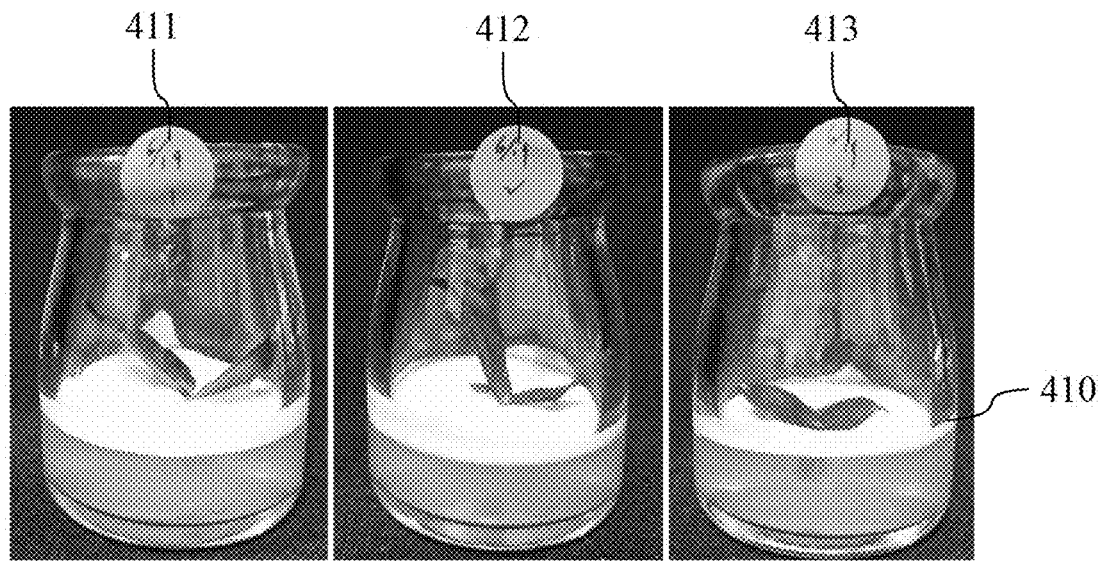
FIGS. 6A, 6B, 6C, 6D and 6E show test results of the isolation microbial growth test according to Example 8 of one embodiment of the present disclosure.
Figure 6B:
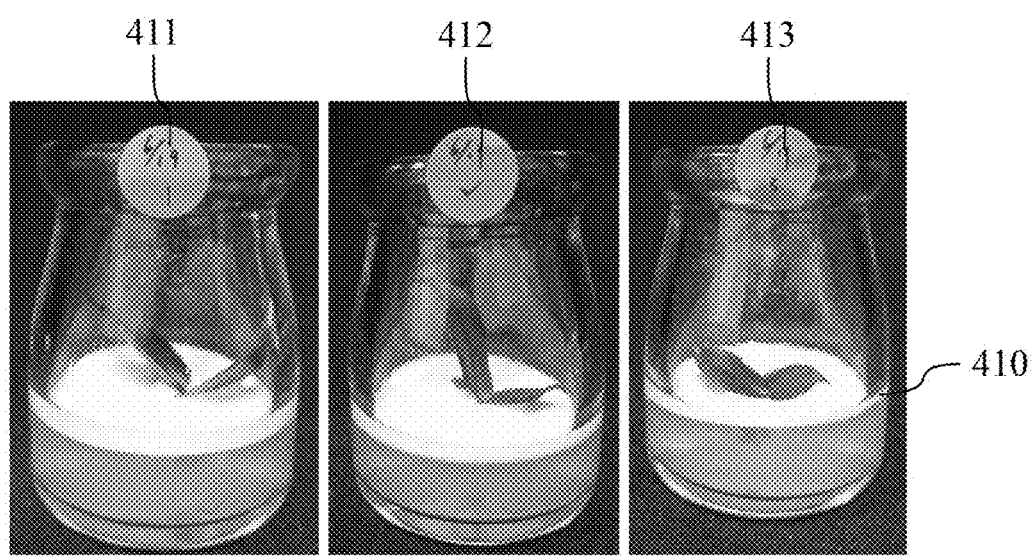
Figure 6C:
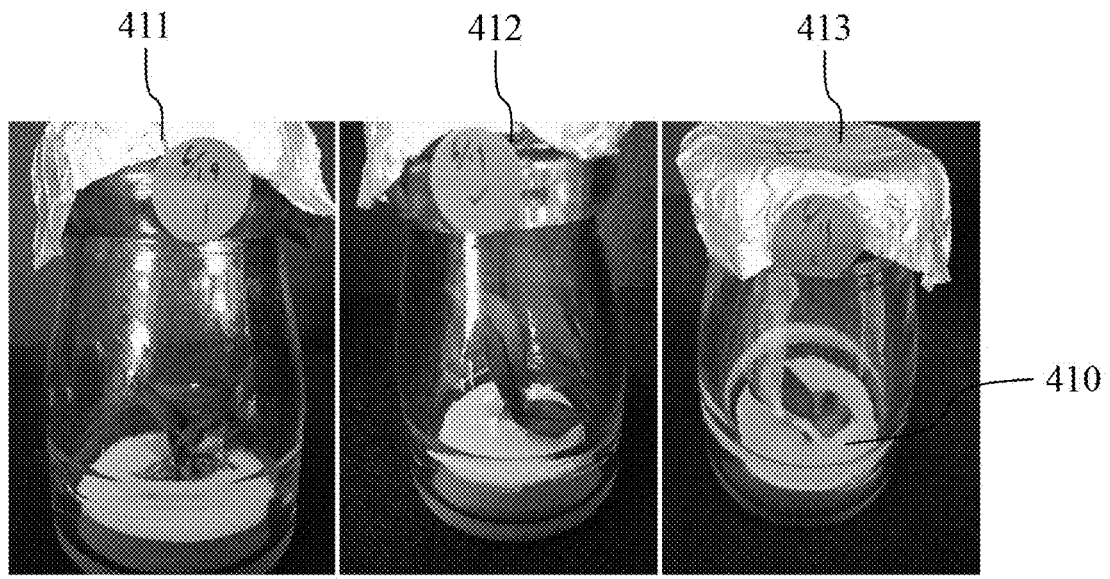
Figure 6D:
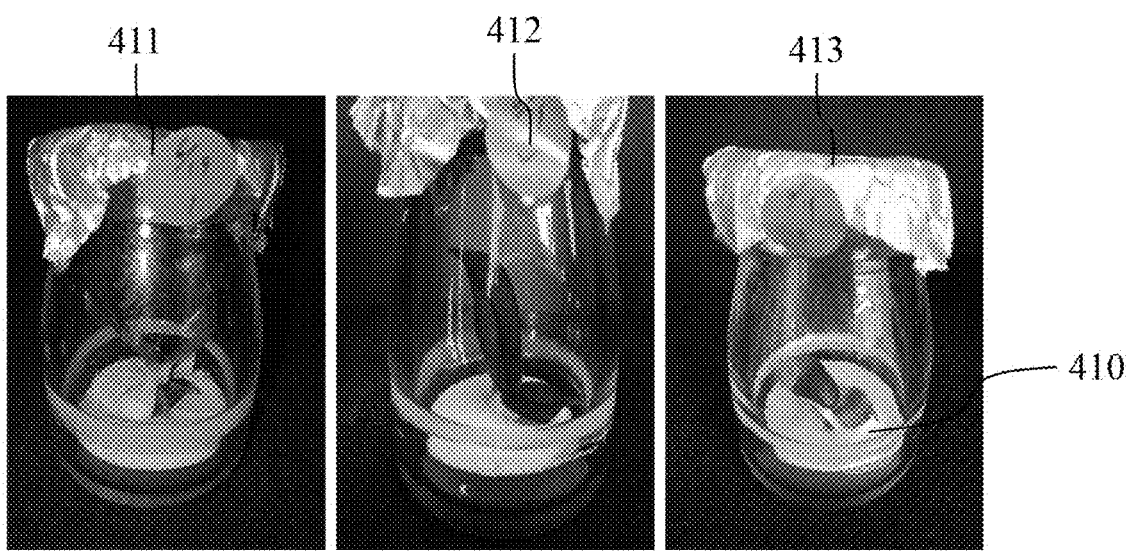
Figure 6E:
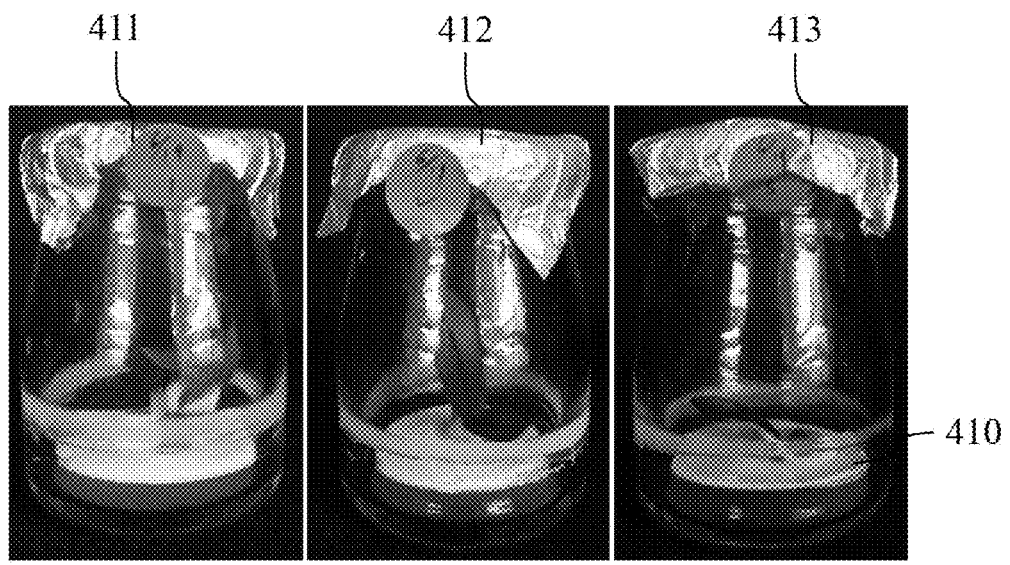

Please refer to FIGS. 6A, 6B, 6C, 6D and 6E, which show test results of the isolation microbial growth test according to Example 8 insulation layer composition 410. In FIGS. 6A to 6E, the tubes from left to right are Example 8 insulation layer composition test group 411, Example 8 insulation layer composition test group 412 and Example 8 insulation layer composition test group 413, wherein FIG. 6A shows the test result on the 1st day, FIG. 6B shows the test result on the 8th day, FIG. 6C shows the test result on the 15th day, FIG. 6D shows the test result on the 22nd day, and FIG. 6E shows the test result on the 29th day. In FIGS. 6B to 6E, the microbial growth cannot be observed in Example 8 insulation layer composition test group 411, Example 8 insulation layer composition test group 412 and Example 8 insulation layer composition test group 413 on the 8th day, the 15th day, the 22nd day and the 29th day, respectively.

Figure 7A:
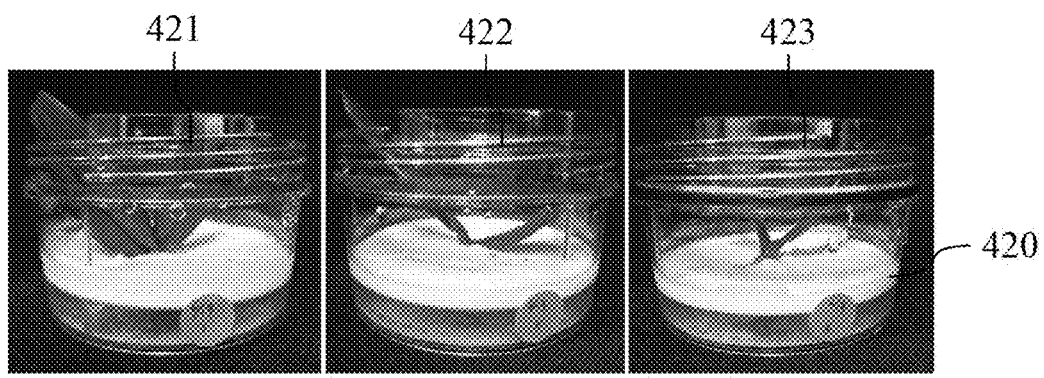
FIGS. 7A, 7B, 7C, 7D and 7E show test results of the isolation microbial growth test according to Example 9 of one embodiment of the present disclosure.
Figure 7B:
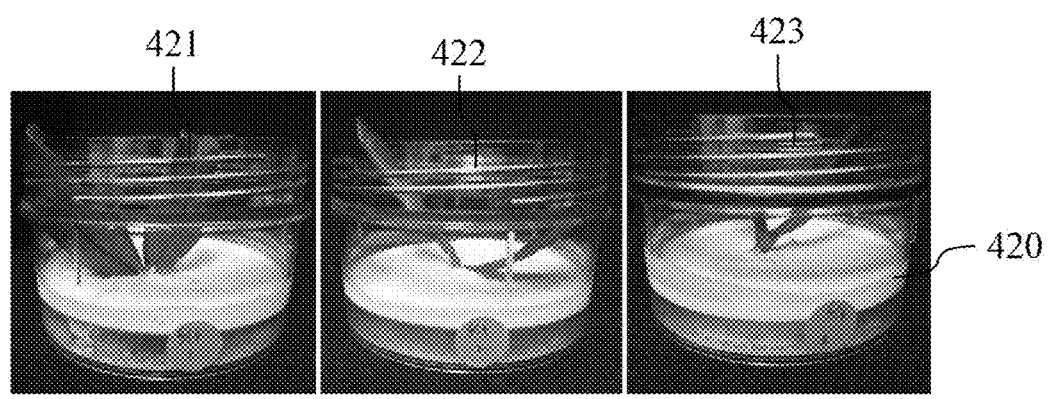
Figure 7C:
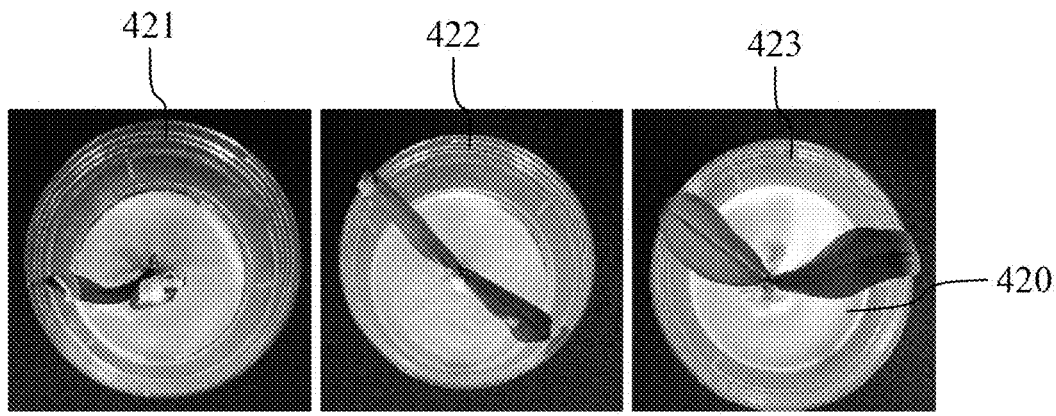
Figure 7D:
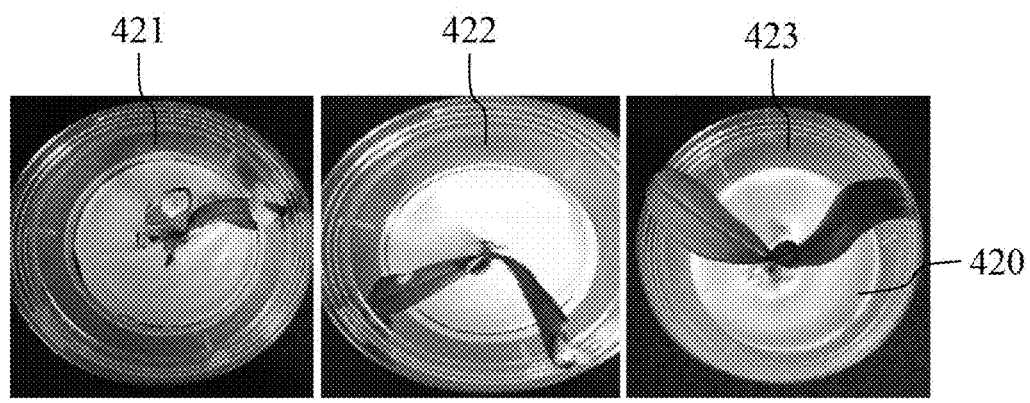
Figure 7E:
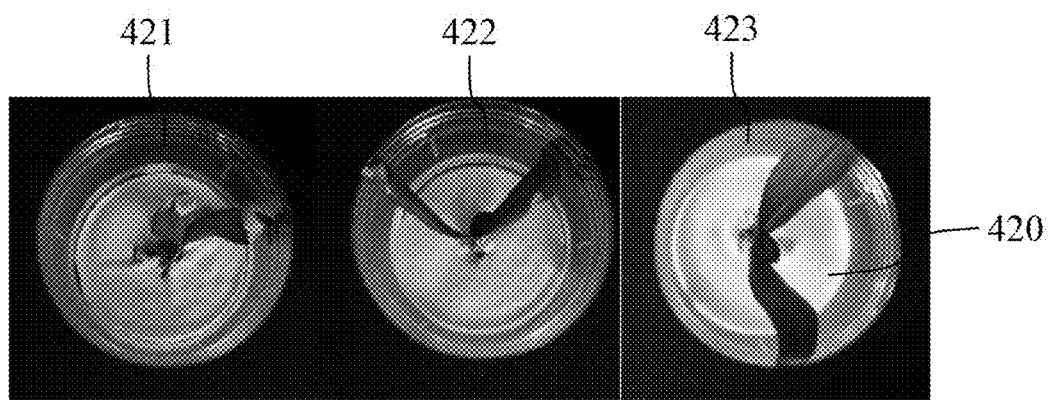

Please refer to FIGS. 7A, 7B, 7C, 7D and 7E, which show test results of the isolation microbial growth test according to Example 9 insulation layer composition 420. In FIGS. 7A to 7E, the tubes from left to right are Example 9 insulation layer composition test group 421, Example 9 insulation layer composition test group 422 and Example 9 insulation layer composition test group 423, wherein FIG. 7A shows the test result on the 1st day, FIG. 7B shows the test result on the 8th day, FIG. 7C shows the test result on the 15th day, FIG. 7D shows the test result on the 22nd day, and FIG. 7E shows the test result on the 29th day. In FIGS. 7B to 7E, the microbial growth cannot be observed in Example 9 insulation layer composition test group 421, Example 9 insulation layer composition test group 422 and Example 9 insulation layer composition test group 423 on the 8th day, the 15th day, the 22nd day and the 29th day, respectively.

The result indicates that the insulation layer composition of the present disclosure can be used as the insulation layer for plant tissue culture, allowing tissue culture plants to grow in the open space, and effectively avoiding bacterial or fungal contamination.

Example 10

In this test example, the plant material is flower of cockscomb, and all operations of the plant tissue culture are performed in the laminar airflow bench. The medium used for the isolation microbial growth test is a ½ MS semi-solid medium with 3% sugar and 0.75% agarose. The test procedure is as follows: the plant material is implanted in the medium for use, and the test group includes 3 tubes, in which each of the tube is implanted into one plant material. Then, the polyvinyl acetate emulsion resin, water, gel forming agent and hyaluronic acid diluent are uniformly mixed in the weight ratio of 2:1:0.5:0.5 to prepare the insulation layer composition of the present disclosure (Example 10 insulation layer composition 510). Example 10 insulation layer composition 510 is then poured into the tube with flower of cockscomb to the thickness of about 0.2 cm to 0.3 cm so that Example 10 insulation layer composition 510 can sufficiently cover the surface of the medium to form the insulation layer. The tissue culture plants covered with Example 10 insulation layer composition 510 are placed in the open space with temperature range of 26° C. to 27° C. to perform the isolate the microbial growth test, and photographed on the 1st day, the 8th day, the 15th day, the 22nd day and the 29th day to observe when microorganisms began to grow.

Figure 8A:
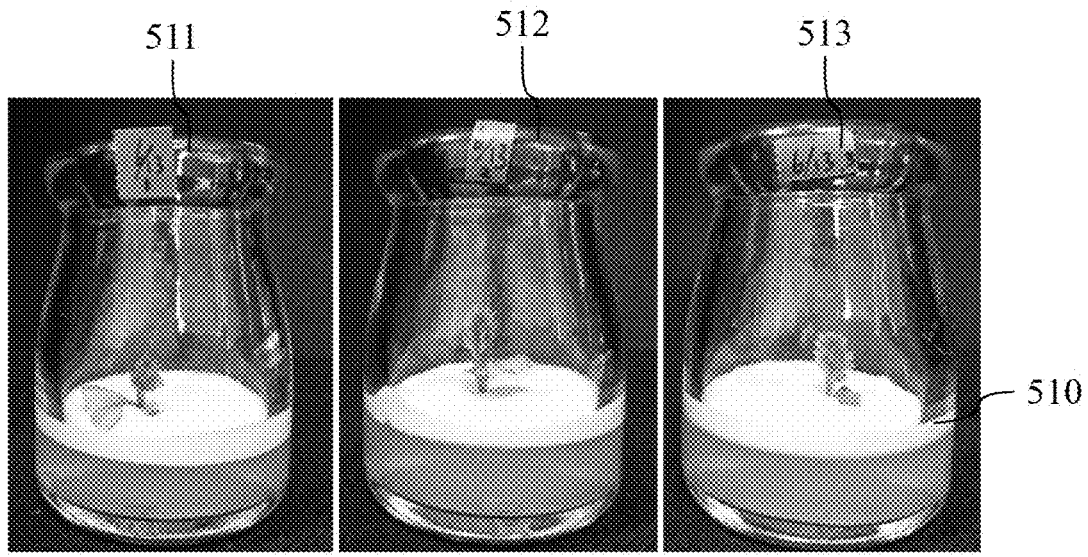
FIGS. 8A, 8B, 8C, 8D and 8E show test results of the isolation microbial growth test according to Example 10 of one embodiment of the present disclosure.
Figure 8B:
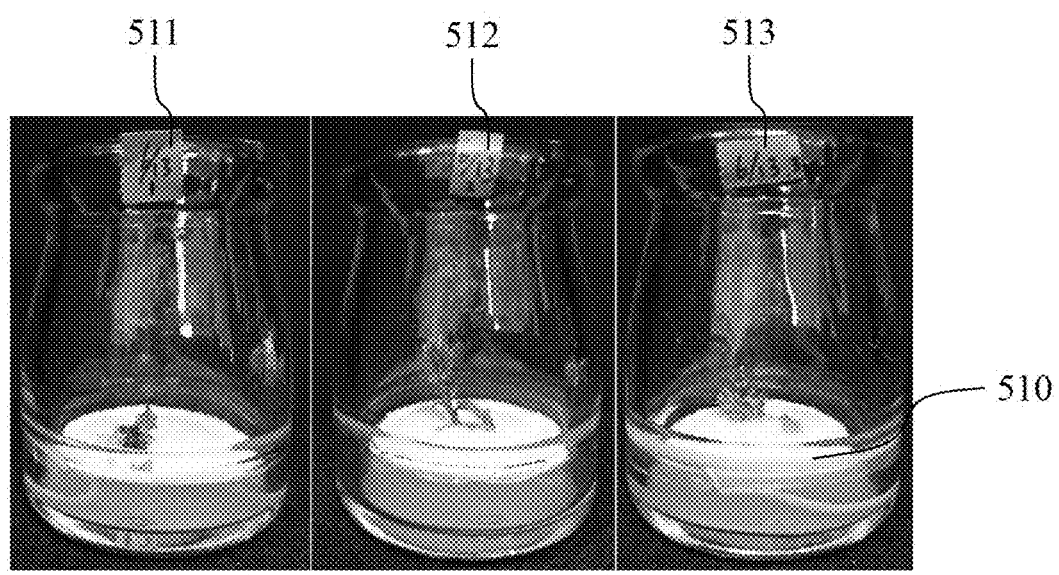
Figure 8C:
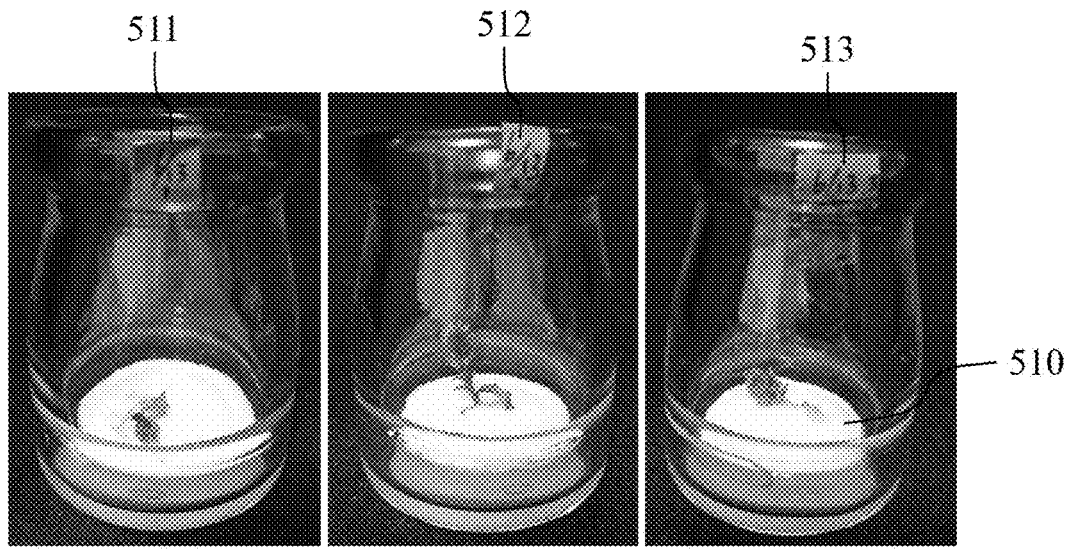
Figure 8D:
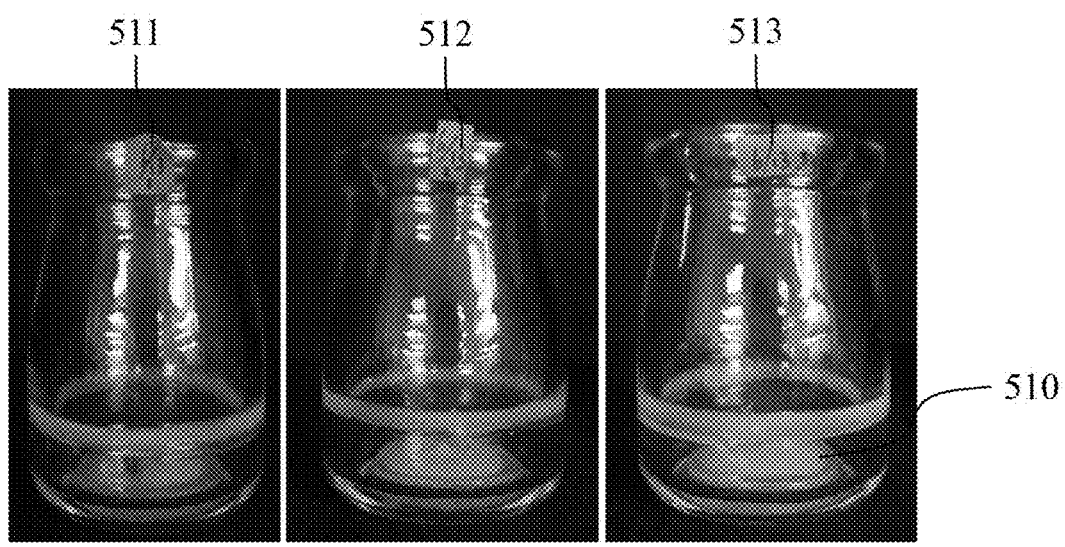
Figure 8E:
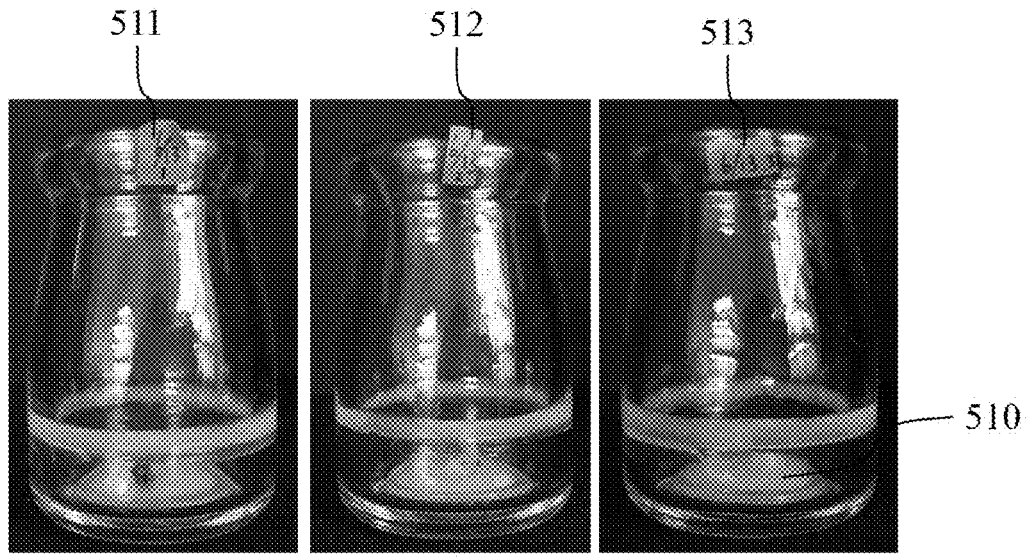

Please refer to FIGS. 8A, 8B, 8C, 8D and 8E, which show test results of the isolation microbial growth test according to Example 10 insulation layer composition 510. In FIGS. 8A to 8E, the tubes from left to right are Example 10 insulation layer composition test group 511, Example 10 insulation layer composition test group 512 and Example 10 insulation layer composition test group 513, wherein FIG. 8A shows the test result on the 1st day, FIG. 8B shows the test result on the 8th day, FIG. 8C shows the test result on the 15th day, FIG. 8D shows the test result on the 22nd day, and FIG. 8E shows the test result on the 29th day. In FIGS. 8B to 8E, the microbial growth cannot be observed in Example 10 insulation layer composition test group 511, Example 10 insulation layer composition test group 512 and Example 10 insulation layer composition test group 513 on the 8th day, the 15th day, the 22nd day and the 29th day, respectively. The result also indicates that the insulation layer composition of the present disclosure can be used as the insulation layer for plant tissue culture, allowing tissue culture plants to grow in the open space, and effectively avoiding bacterial or fungal contamination.

Example 11

In this test example, the plant material is leave of *Eucalyptus*, and all operations of the plant tissue culture are performed in the laminar airflow bench. The medium used for the isolation microbial growth test is a ½ MS semi-solid medium with 3% sugar and 0.75% agarose. The test procedure is as follows: the plant material is implanted in the medium for use, and the test group includes 3 tubes, in which each of the tube is implanted into one plant material. Then, the polyvinyl acetate emulsion resin, water, gel forming agent and hyaluronic acid diluent are uniformly mixed in the weight ratio of 2:1:0.5:0.5 to prepare the insulation layer composition of the present disclosure (Example 11 insulation layer composition 610). Example 11 insulation layer composition 610 is then poured into the tube with leave of *Eucalyptus* to the thickness of about 0.2 cm to 0.3 cm so that Example 11 insulation layer composition 610 can sufficiently cover the surface of the medium to form the insulation layer. The tissue culture plants covered with Example 11 insulation layer composition 610 are placed in the open space with temperature range of 26° C. to 27° C. to perform the isolate the microbial growth test, and photographed on the 1st day, the 8th day, the 15th day, the 22nd day and the 29th day to observe when microorganisms began to grow.

Figure 9A:
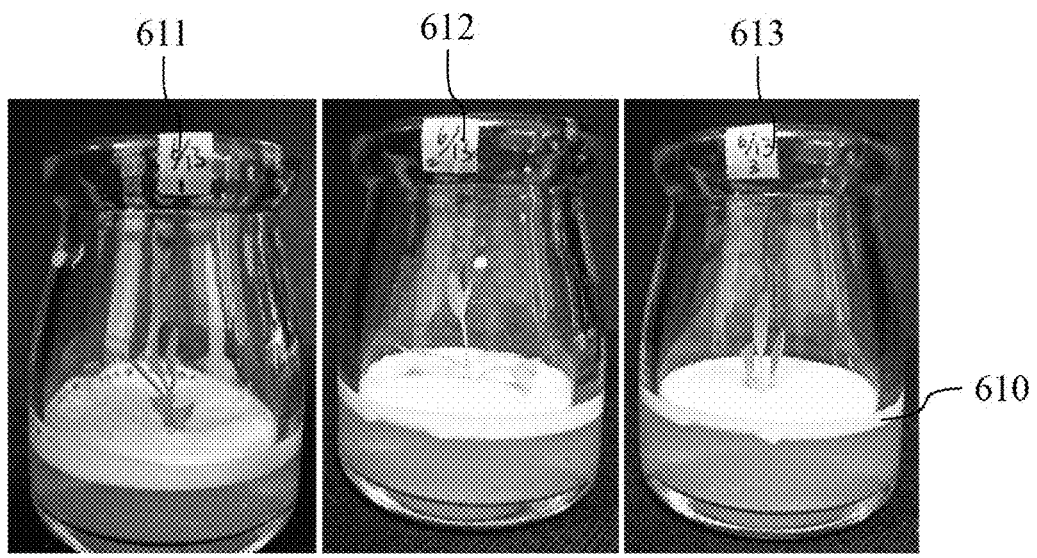
FIGS. 9A, 9B, 9C, 9D and 9E show test results of the isolation microbial growth test according to Example 11 of one embodiment of the present disclosure.
Figure 9B:
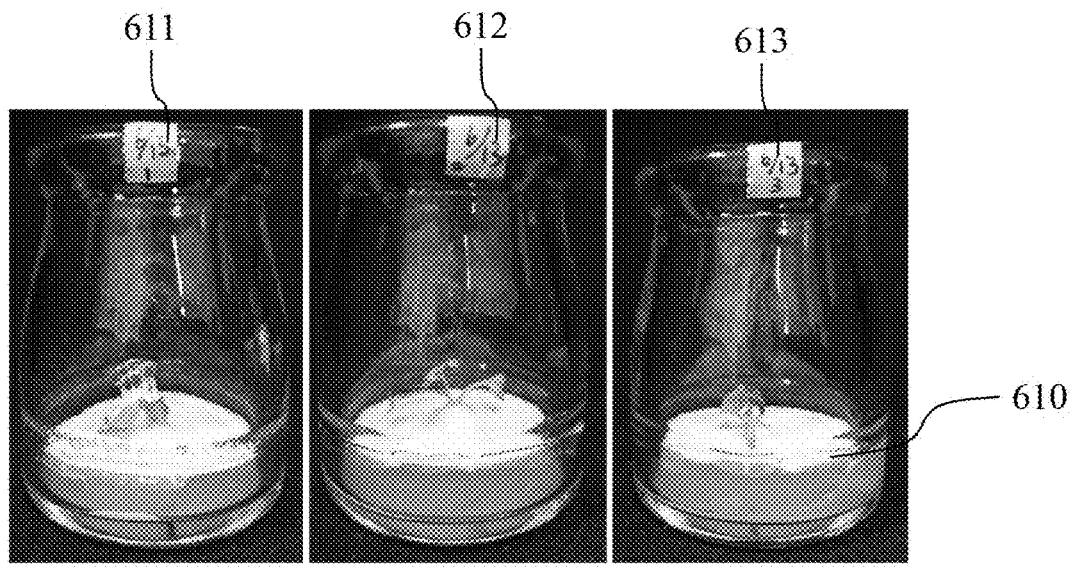
Figure 9C:
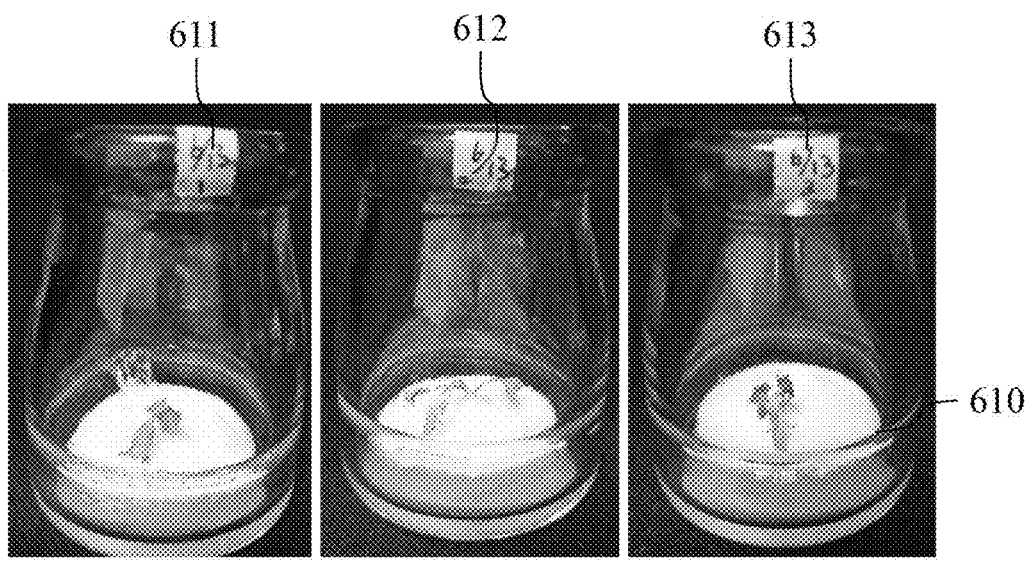
Figure 9D:
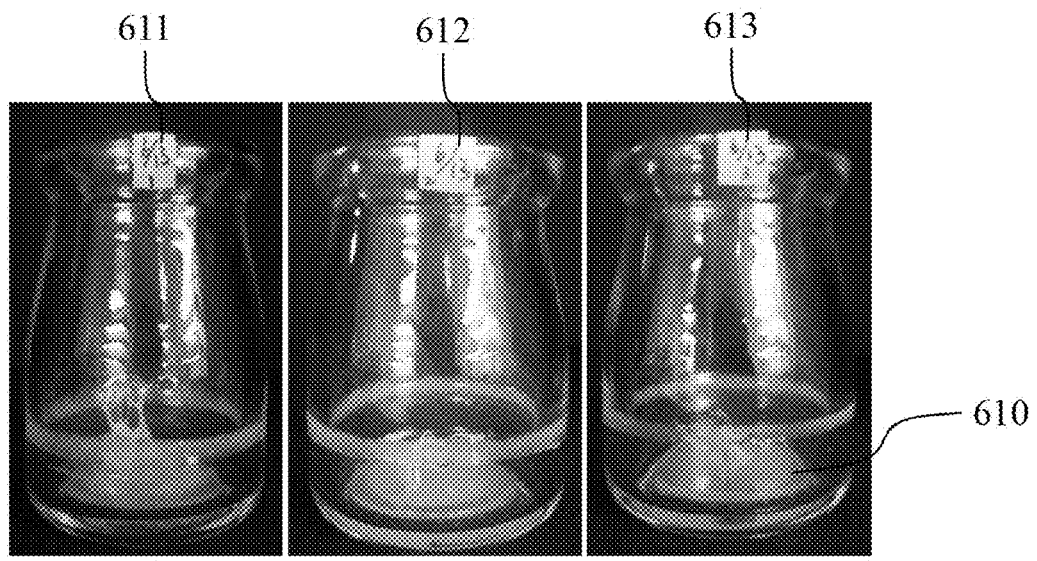
Figure 9E:
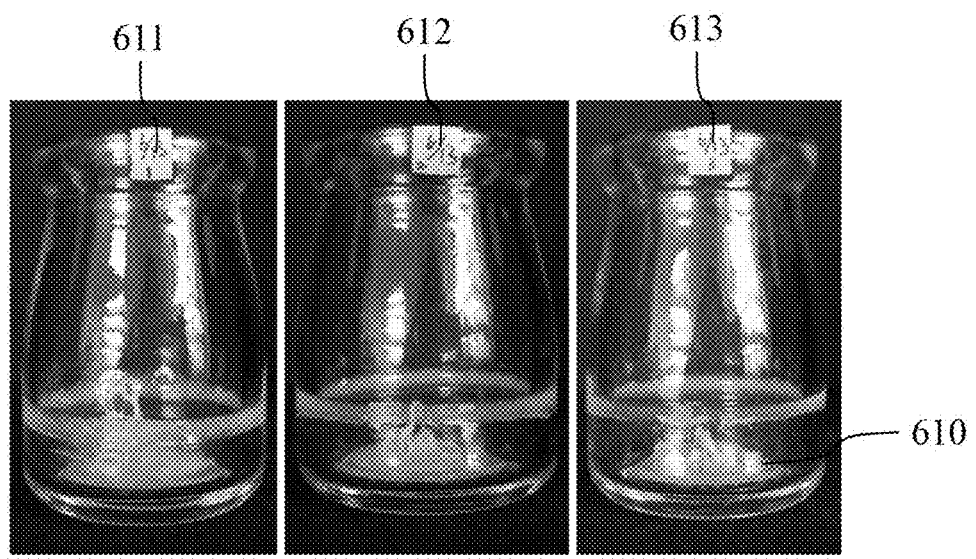

Please refer to FIGS. 9A, 9B, 9C, 9D and 9E, which show test results of the isolation microbial growth test according to Example 11 insulation layer composition 610. In FIGS. 9A to 9E, the tubes from left to right are Example 11 insulation layer composition test group 611, Example 11 insulation layer composition test group 612 and Example 11 insulation layer composition test group 613, wherein FIG. 9A shows the test result on the 1st day, FIG. 9B shows the test result on the 8th day, FIG. 9C shows the test result on the 15th day, FIG. 9D shows the test result on the 22nd day, and FIG. 9E shows the test result on the 29th day. In FIGS. 9B to 9E, the microbial growth cannot be observed in Example 11 insulation layer composition test group 611, Example 11 insulation layer composition test group 612 and Example 11 insulation layer composition test group 613 on the 8th day, the 15th day, the 22nd day and the 29th day, respectively. The result also indicates that the insulation layer composition of the present disclosure can be used as the insulation layer for plant tissue culture, allowing tissue culture plants to grow in the open space, and effectively avoiding bacterial or fungal contamination.

In conclusion, the insulation layer composition of the present disclosure includes polyvinyl acetate emulsion resin, water, a gel forming agent and a hyaluronic acid diluent, which can be used as the insulation layer for plant tissue culture. The insulation layer composition can be covered on a plant tissue culture medium for effectively isolating the contact between the culture medium and the microorganisms, so that the tissue culture plant can be cultured in the open space without being contaminated by bacteria or fungi for up to 63 days. In addition, the insulation layer composition of the present disclosure can also improve the condition in which the culture medium of the plant tissue culture is dry-cracked when it is placed in the open space for a long period of time due to evapotranspiration or absorption of moisture or nutrients by the root of the plant. Therefore, the insulation layer composition of the present disclosure has the potential to be applied to plant tissue culture.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An insulation layer composition comprising a polyvinyl acetate emulsion resin, water, a gel forming agent and a hyaluronic acid diluent, wherein the gel forming agent is a mixture of glycerin and polyglycerol acrylate.

2. The insulation layer composition of claim 1, wherein a volume percent concentration (V/V) of the hyaluronic acid diluent is 1%.

3. The insulation layer composition of claim 2, wherein the polyvinyl acetate emulsion resin, the water, the gel forming agent and the hyaluronic acid diluent are mixed in a weight ratio of 2:1:0.5:0.5 to 2:2:1:1.

4. The insulation layer composition of claim 3, wherein the polyvinyl acetate emulsion resin, the water, the gel forming agent and the hyaluronic acid diluent are mixed in a weight ratio of 2:1:0.5:1.

5. The insulation layer composition of claim 3, wherein the polyvinyl acetate emulsion resin, the water, the gel forming agent and the hyaluronic acid diluent are mixed in a weight ratio of 2:1:0.5:0.5.

6. The insulation layer composition of claim 3, wherein the polyvinyl acetate emulsion resin, the water, the gel forming agent and the hyaluronic acid diluent are mixed in a weight ratio of 2:1.5:0.7:0.6.

7. An insulation layer for a plant tissue culture, comprising:
the insulation layer composition of claim 1.

8. The insulation layer for the plant tissue culture of claim 7, wherein the insulation layer is used to isolate a medium from contact with a source of contamination.

9. The insulation layer for the plant tissue culture of claim 8, wherein the source of contamination is a microorganism.

10. The insulation layer for the plant tissue culture of claim 9, wherein the microorganism is a fungus or a bacterium.

* * * * *